US006322530B1

(12) United States Patent
Johnson, Jr. et al.

(10) Patent No.: US 6,322,530 B1
(45) Date of Patent: Nov. 27, 2001

(54) PNEUMATIC ACHILLES WRAP

(75) Inventors: Glenn W. Johnson, Jr., Summit; Henry J. McVicker, Madison, both of NJ (US)

(73) Assignee: Aircast, Inc., Summit, NJ (US)

( * ) Notice: Subject to any disclaimer, the term of this patent is extended or adjusted under 35 U.S.C. 154(b) by 0 days.

(21) Appl. No.: 08/745,276

(22) Filed: Nov. 8, 1996

(51) Int. Cl.[7] .............. A61F 13/00; A61F 5/00; A61H 9/00
(52) U.S. Cl. ................ 602/65; 602/27; 602/13; 601/151; 128/DIG. 20
(58) Field of Search ................ 602/5, 13, 27, 602/23, 60–62, 65, 6; 128/882, DIG. 20; 601/152, 151

(56) References Cited

U.S. PATENT DOCUMENTS

| D. 343,002 | 1/1994 | Gauvry . | |
|---|---|---|---|
| 4,266,298 | * 5/1981 | Graziano | 2/22 |
| 4,372,297 | * 2/1983 | Perlin | 601/151 |
| 4,628,945 | 12/1986 | Johnson, Jr. . | |
| 4,702,232 | * 10/1987 | Gardner et al. | 601/152 |
| 4,841,957 | 6/1989 | Wooten et al. . | |
| 4,842,956 | 6/1989 | Gardner et al. . | |
| 4,977,891 | 12/1990 | Grim . | |
| 5,135,473 | * 8/1992 | Epler et al. | 602/65 |
| 5,348,530 | 9/1994 | Grim et al. . | |
| 5,354,260 | 10/1994 | Cook . | |
| 5,443,440 | 8/1995 | Tumey et al. . | |
| 5,464,385 | * 11/1995 | Grim | 602/27 |
| 5,475,935 | 12/1995 | Frost . | |
| 5,613,941 | 3/1997 | Prengler . | |
| 5,711,760 | * 1/1998 | Ibrahim et al. | 601/152 X |
| 5,833,636 | * 10/1998 | Yokoi | 602/5 |
| 5,843,010 | * 12/1998 | Bodmer | 602/65 X |

FOREIGN PATENT DOCUMENTS

| 817521 | 7/1959 | (GB) . |
|---|---|---|
| WO9808470 | 3/1998 | (WO) . |

OTHER PUBLICATIONS

"Modulation of Tendon Healing by Nitric Oxide"; Gac et al., 41st Annual Meeting, Orthopedic Research Society, Feb. 13–16, 1995, p. 219–PS.

"Pulsing Pneumatic Compression in an Aircast™ Leg Brace", Glen W. Johnson, Jr., May 22, 1983.

* cited by examiner

Primary Examiner—Denise Pothier
(74) Attorney, Agent, or Firm—Jones, Day, Reavis & Pogue

(57) ABSTRACT

The pneumatic Achilles wrap comprises a wrap including at least one strap for fastening the wrap around the foot and around the ankle. The wrap positions an arch cell which contains a dynamic volume of air within the wrap under a human foot. The arch cell is fabricated from a flexible material and is in communication with a conduit member. Upon application of external pressure to the arch cell, air is expelled from said air cell through said conduit member. The wrap also positions a tendon cell which contains a dynamic volume of air within the wrap against the Achilles tendon. The tendon cell is in communication with the arch cell via the conduit member. The tendon cell is also fabricated from a flexible material. Upon the expelling of air from said arch cell, the air enters through the conduit member into the tendon cell which exerts a greater pressure against the Achilles tendon.

41 Claims, 3 Drawing Sheets

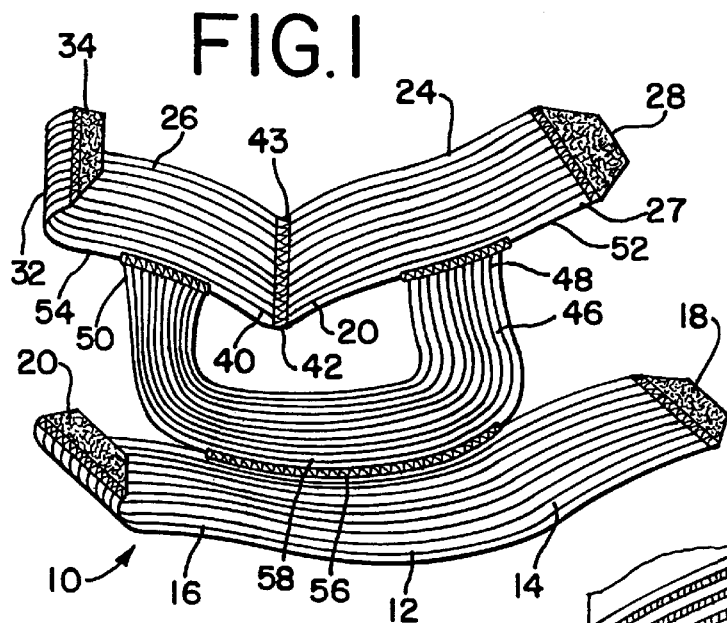
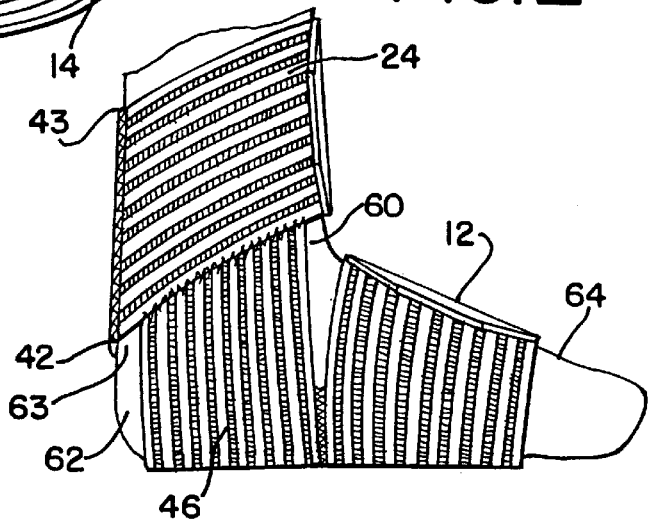
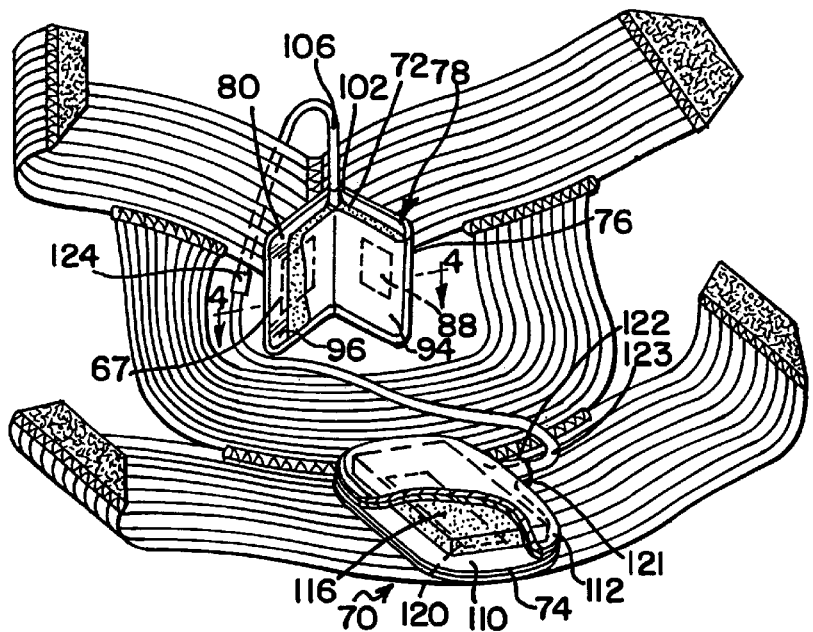

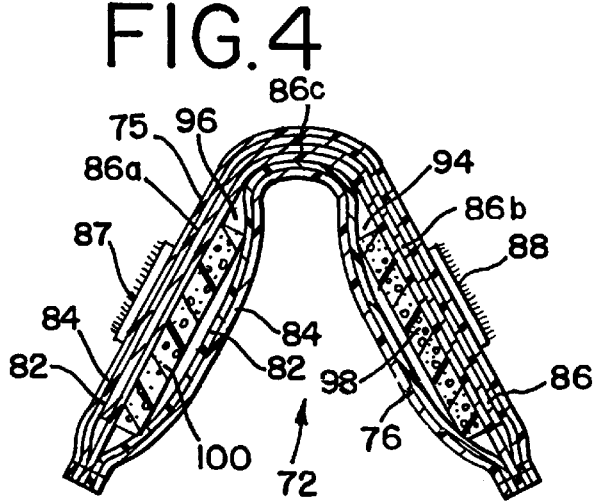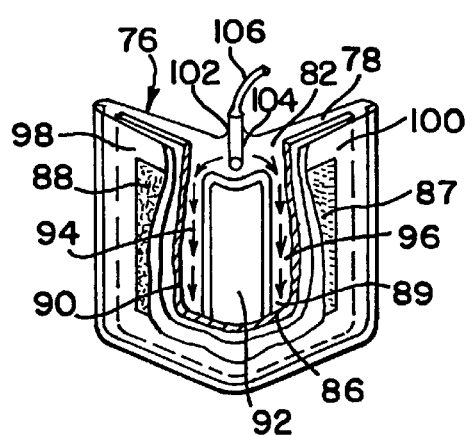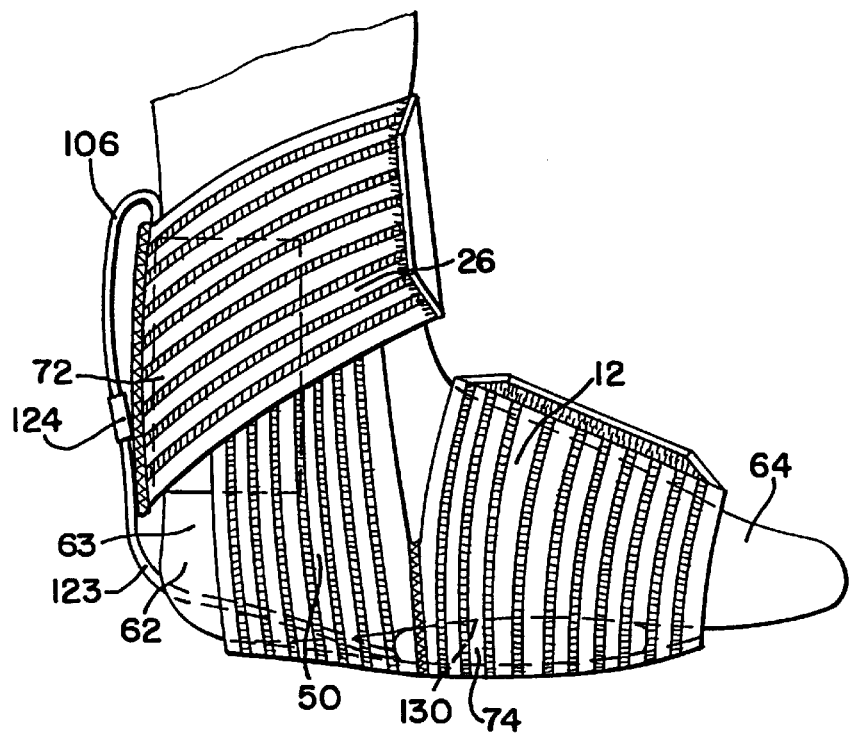

PNEUMATIC ACHILLES WRAP

BACKGROUND

1. Field of the Invention

This invention relates to a compression wrap for pneumatically applying dynamic pressure to the Achilles tendon.

2. Description of Related Art

Active people commonly experience the ache and debilitating effects of posterior heel pain as a result of three commonly accepted causes: Haglund syndrome, Achilles tendinitis/osis and Sever's disease.

Haglund syndrome is characterized by a painful soft tissue swelling where the Achilles tendon attaches to the calcaneum (heel bone). Haglund syndrome can often result in the development of a bony deposit on the back of the calcaneum or in the inflammation of the bursa, the fluid filled sac that decreases friction between the Achilles tendon and the calcaneum, which is known as retrocalcaneal bursitis. It is believed that Haglund syndrome results from the repetitive application of trauma or stress to the Achilles tendon.

Achilles tendinitis and tendinosis describe two classifications of tendon injury around the Achilles. Tendinosis refers to non-inflammatory intratendinous degeneration which is initially asymptomatic. Tendinitis describes symptomatic degeneration of the tendon associated with inflammation. Stanish has referred to these tendon classifications as non-union soft-tissue injuries. It is believed that non-union soft-tissue injuries are caused by inadequate perfusion of the local tissues. The affliction is characterized by soft tissue swelling, tenderness to the touch and roughening about the Achilles tendon known as crepitus. Those suffering from Achilles tendinitis/osis also experience pain with active pointing and passive raising of the foot.

Sever's disease results from a sclerosis or thickening and irregularity of the growth plate known as the calcaneal apophysis. It is believed that Sever's disease results from inflammation of the soft tissues of the heel following an injury. Sever's disease may cause a number of conditions including retrocalcaneal bursitis, traction apophysitis, which is the separating of the tendon from the bone, and osteochondrosis of the calcaneal apophysis which is irritation and inflammation of the bone and cartilage in the heel. Those suffering from Sever's disease experience pain down the back of the heel with passive raising of the foot, rapid and repetitive pointing of the foot and a springly gait. Sever's disease is aggravated by running and jumping.

These conditions are often treated by use of heel lifts which normally are foam pads approximately 0.25 inches thick; oral pain relievers; shoe inserts; anti-inflammatory medications; rest; ultrasound; various physical therapy treatments; and flexibility exercises. Surgical procedures such as diagonal removal of a heel bone known as oblique calcaneal osteotomy; removal of a deep and superficial retrocalcaneal bursae; cleaning and tendon repair are sometimes required for effective treatment.

U.S. Pat. No. 4,841,957 in the name of Wooten, et al. describes a U-shaped pad for applying compression around the affected area of the heel. However, the device disclosed in the Wooten patent only applies static pressure to the affected area of the Achilles tendon. We have reason to believe that a dynamic pulsating pressure would be more effective in remedying maladies associated with the Achilles tendon.

Nitric oxide is known to be released with a change in sheer stress in blood flow against the endothelial cells lining the veins. Our studies indicate that pulsating pressure accelerates venous velocity. Other studies show that acceleration of venous velocity increases sheer stress. A recent study, *Modulation of Tendon Healing by Nitric Oxide*, authored by George A. C. Murrell and others indicates that nitric oxide is present during tendon healing, and that the inhibition of nitric oxide reduces the healing response. While the tendons are avascular, the small nitric oxide molecule is known to pass through vessel walls. Nitric oxide acts as a vasodilator, providing greater fluid and nutrition to local tissues.

The results indicated by testing the present invention supports the belief that application of a dynamic, pulsating pressure around the sides of the Achilles tendon provides relief and healing to those suffering from maladies afflicting the Achilles tendon.

United Kingdom patent No. 817,521 discloses an apparatus for facilitating the blood circulation in the extremities of the human body. The device shown in this patent is cumbersome making the same difficult and time consuming to attach to the lower leg of the wearer. A further disadvantage in the use of this device resides in the fact that the inflatable cushions must be inflated from an external source, such as a pump.

U.S. Pat. No. 5,348,530 discloses a pneumatic ankle brace with a bladder and foot pump arrangement. The device of this patent is of rather complicated construction and requires use of a detachable hand-held pump.

U.S. Pat. No. 4,841,956 discloses a device adapted to be mounted to the lower leg and foot of a person for inducing venous blood flow in the leg. This device includes a pulse generator and programmable distributor necessitating a non-ambulatory position for the wearer during use.

U.S. Pat. No. 4,628,945 discloses a self-inflating ankle brace including air bags with resilient, compressible filler material. This patent discloses only a brace.

SUMMARY OF THE INVENTION

The present invention provides relief to those who are suffering from posterior heel pain.

Therefore, an object of the invention is to provide an Achilles wrap which includes a device for applying pulsating pressure to the Achilles tendon.

Another object of the invention is to utilize a foot cell to pulse pump pressure to the area around the Achilles tendon.

A further object of the invention is to provide an Achilles wrap which provides pulsating pressure to the Achilles tendon by use of a V-shaped pad which envelopes the Achilles tendon.

An even further object of the invention is to utilize an ankle wrap made of a flexible, stretchable material to which a strip of a plurality of hooks can easily attach, so that strips of a plurality of hooks attached to an arch cell and an Achilles tendon cell can be used to locate the arch cell and tendon cell anywhere on the ankle wrap to facilitate positioning.

The foregoing advantages are achieved by the pneumatic Achilles wrap of the present invention. The Achilles wrap comprises a wrap including at least one strap for fastening the wrap around the foot and around the ankle. The wrap is preferably made of a stretchable, flexible material to which a strip of a plurality of hooks readily attaches. The wrap positions an arch cell which contains a dynamic volume of air within the wrap under the arch of the foot. The arch cell preferably includes a strip of a plurality of hooks for attachment to the wrap. The arch cell is fabricated from a flexible material and is in communication with a conduit member. The tendon cell is preferably V-shaped to envelop the Achilles tendon and includes a strip of a plurality of hooks for attachment to the wrap. Upon application of external pressure to the arch cell, air is expelled from said air cell through the conduit member.

Both the tendon cell and the arch cell are fabricated from a flexible material defining pockets containing open-cell foam pads. Upon the expelling of air from said arch cell, the air passes through the conduit member into the tendon cell which exerts a greater pressure against the Achilles tendon. The arch and tendon cells are self-inflating. Thus, an external pump is not required.

The present invention in its various aspects has only been summarized briefly. For a better understanding of the present invention and its objects and advantages, reference should be made to the following detailed description taken in conjunction with the accompanying drawings.

BRIEF DESCRIPTION OF THE DRAWINGS

The drawings which are part of the disclosure illustrate the present invention.

FIG. 1 is a perspective view of the wrap assembly of the present invention.

FIG. 2 is a side elevational view of the wrap assembly of FIG. 1 wrapped around a human foot.

FIG. 3 is a perspective view of the wrap assembly of FIG. 1 including the pneumatic system of the present invention with portions cut away for illustrative purposes.

FIG. 4 is a cross-sectional view of an Achilles tendon cell taken along line 4—4 in FIG. 3.

FIG. 5 is a cut away view of the tendon cell of the present invention.

FIG. 6 is a side view of the present invention shown in FIG. 3 wrapped around the human foot with the pneumatic system in partial phantom.

DETAILED DESCRIPTION OF THE INVENTION

Figure 7:
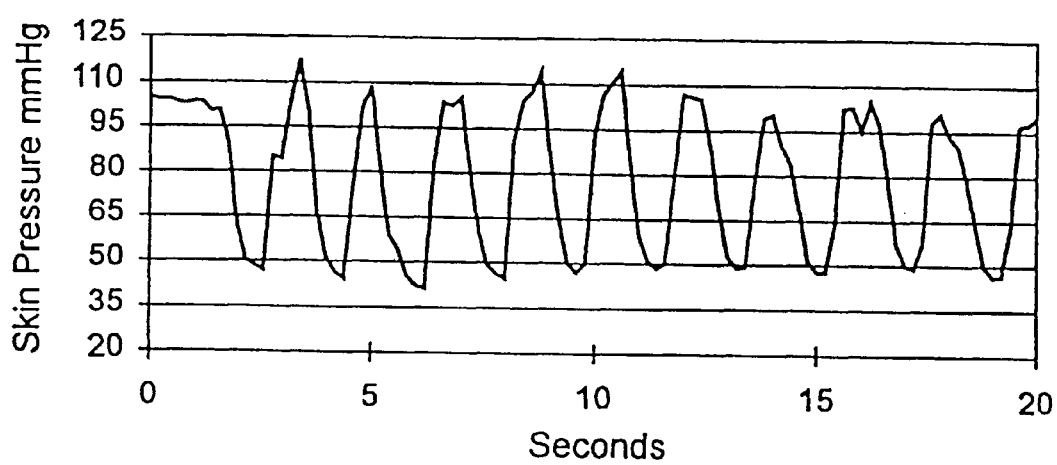
FIG. 7 is a graph of the pressure the present invention applies to the Achilles tendon.

The present invention comprises an Achilles wrap which accommodates a pneumatic system. FIG. 1 depicts the Achilles wrap 10 of the present invention which can be worn on either foot of a human being. The Achilles wrap 10 is made up of a woven filament material which is flexible, stretchable and adaptable to attachable engagement by a plurality of hooks, such as VELCRO hooks. The Achilles wrap 10 comprises four separate straps.

A foot strap 12 is the longest of the straps, with a first end 14 and a second end 16. A tab 18 containing a plurality of hooks, such as VELCRO hooks, is connected and preferably stitched to the first end 14 of the foot strap 12 with the hooks facing inwardly. A tab 20 is connected and preferable stitched to the second end 16 of the foot strap 12 which also contains a plurality of hooks which face outwardly.

The Achilles wrap 10 also includes a first ankle strap 24 and a second ankle strap 26. The first ankle strap has a first end 27 to which a tab 28 with a plurality of hooks such as VELCRO hooks facing inwardly is connected and preferably stitched. The second ankle strap 26 has a first end 32 to which a tab 34 containing a plurality of hooks facing outwardly is connected and preferably stitched. The first ankle strap 24 and the second ankle strap 26 both have second ends 38, 40 connected and preferably stitched to each other at an obtuse angle defining a lower vertex 42 and upper vertex of 43.

The Achilles wrap 10 further includes a heel strap 46 which has a first end 48 and a second end 50. The first end 48 of the heel strap 46 is connected and preferably stitched to a proximal side 52 of the first ankle strap 24. The second end 50 of the heel strap 46 is connected and preferably stitched to a proximal side 54 of the second ankle strap 26. The foot strap 12 has a proximal side 56, the central portion of which is connected and preferably stitched to a central portion of a distal side 58 of the heel strap 46.

The relationship of all the straps in the Achilles wrap 10 is configured to accommodate the ankle 60, the heel 62, the Achilles tendon 63 and the left or right foot 64 of a human being as shown in FIG. 2. The plurality of hooks contained on each of the tabs 18, 20, 28, 34 are disposed to facilitate engagement of the hooks on the tabs to the woven filament material comprising the respective straps 12, 24, 26. The foot strap 12 and the ankle straps 24, 26 are fastened around the foot 64 and ankle 60, respectively, to secure the Achilles wrap 10 on the foot. The angled relationship of the first and second ankle straps 24, 26 facilitate the upper vertex 43 to contact a heel 62 at a lower elevation than the top side of the foot 64 where the first end 27 of the first ankle strap 24 and the first end 32 of the second ankle strap 26 come together as shown in FIG. 2.

The pneumatic system 70 shown in FIG. 3 comprises an Achilles tendon cell 72 and an arch cell 74 in connection with each other. As shown best in FIG. 4 the tendon cell 72 comprises a first wall 75 and a second wall 76 each made of plastic. Each wall of the tendon cell is preferably made of a polyurethane coating 82 applied to a nylon ply 84. The two walls 75, 76 are sealed together with the polyurethane coating 82 inside along the common edges thereof on all but one side, preferably by radio frequency welding, to form a bi-fold pocket 78. The pocket 78 in the tendon cell 72 contains a generally V-shaped metal support 86 which is sufficiently ductile to allow adjustment of the angle defined by the legs of the support 86. As seen in FIG. 4, the support includes leg portions 86a and 86b joined by a medial vertex portion 86c. Of course, the support 86 can be considered as U-shaped.

The nylon ply 84 of the first wall 75 and the second wall 76 comprised of the nylon plies is fuzzy to the touch. Two strips 87, 88 of a plurality of hooks such as VELCRO hooks are attached to the nylon ply 84 of the first wall 75 to facilitate attachment of the tendon cell 72 to the woven filament material of the first ankle strap 24 and the second ankle strap 26, respectively. The Achilles tendon cell 72 takes on the folded shape of the V-shaped support 86 and thereby can receive the heel 62 of a human foot 64.

Referring to FIG. 5 which shows a rear cut-away view of the tendon cell 72, a plastic film overlay 89, which preferably comprises transparent polyurethane, is sealed, preferably by radio frequency welding, along a seam 90 to the polyurethane coating 82 of the second wall 76. The seam 90 isolates a medial non-inflatable or uninflated zone 92 between a first lateral compartment 94 and a second lateral compartment 96. Both the compartment 94 and the compartment 96 are in communication with each other, and each contains an open-cell foam 98, 100 of about 0.2 inches thick which provides self-inflation and cushioning features. The seam 90 hermetically seals the overlay 89 to the polyurethane coating 82 of the second wall 76 to form air-tight lateral compartments 94, 96.

The second wall 76 of the tendon cell 72 contains a first neck portion 102. The transparent plastic film overlay 89 has a second neck portion 104 which is registered with and is sealed to the first neck portion 102 with a tunnel therebetween for receiving an inlet tube 106. The inlet tube 106 is hermetically secured between the first neck portion 102 and the second neck portion 104 and serves as a duct to bring air into the medial and lateral compartments 94, 96 of the tendon cell 72.

The arch cell 74, best shown in FIG. 3, comprises two generally oval or elliptical walls, a base wall 110 and a top wall 112, each made from the same material as the walls 75, 76 of the tendon cell 72. Thus, each wall 110, 112 has an inner polyurethane coating applied to an outer nylon ply. The outer surface of the base wall 110 of the arch cell 74 has a strip 116 of a plurality of hooks, such as VELCRO hooks, attached thereto for detachable engagement of the arch cell with the woven filament material of one of the straps. Hence, the arch cell 74 can be secured anywhere on the Achilles wrap 10; the arch cell is preferably secured to the central upper portion of the foot strap 12. The inner polyurethane coating on the top wall 112 is sealed to the inner polyurethane coating on the base wall 110 around the edges thereof to provide a hermetically sealed pocket. The arch cell 74 contains an open-cell foam pad 120 of about 0.5 inches thick. The foam pad 120 is self-inflating, as disclosed in U.S. Pat. No. 4,628,945 referred to above which is assigned to the assignee of the present invention, and which is incorporated herein by reference.

The base wall 110 and the top wall 112 of the arch cell 74 each has corresponding neck portions 121, 122 sealed to each other with a tunnel therein for hermetically receiving an outlet tube 123. The outlet tube 123 is removably coupled by a connector 124 to the inlet tube 106 to provide an air-tight pneumatic system comprising the arch cell 74 and the tendon cell 72.

The Achilles wrap 10 with the arch cell 74 and the tendon cell 72 attached thereto are wrapped around the foot 64 as shown in FIG. 6. The inlet tube 106 and the outlet tube 123 should be positioned along the inside of the foot 64. When weight from the foot 64 bears upon the arch cell 74, air is quickly expelled from the arch cell 74 to the tendon cell 72 to increase the pressure on the Achilles tendon 63. When weight on the arch cell 74 is removed, the self-inflating foam pad 120 in the arch cell 74 expands the walls 110, 112 of the arch cell 74 to increase the volume of the arch cell 74. The increased volume creates a vacuum which quickly sucks air from the tendon cell 72 back into the arch cell 74 thereby decreasing the pressure that the tendon cell 72 bears on the Achilles tendon 63.

Walking while wearing the Achilles wrap 10 produces a rapid change in pressure which enhances the magnitude of the pulsation on the sides of the heel 62, thereby increasing the velocity of blood flow in the foot 64 and the leg. This results in an increase in vascular sheer stress and, we believe, the release of nitric oxide. Hence, the pulsating compression at the sides of the heel 62 may enhance diffusion of nitric oxide into the Achilles tendon 63. The pulsating pressure applied by the tendon cell 72 to the Achilles tendon 63 while walking is shown in FIG. 7. The abscissa represents skin pressure in mmHg; the ordinate represents walking time in seconds.

The arch cell 74 fits into the arch 130 of the foot 64 between the tarsal head and the calcaneus metatarsal. Confining the arch cell 74 to this portion of the foot facilitates insertion of the foot with the wrap 10 in the wearer's shoe and permits the arch cell to function as a dynamic orthotic comfortably supporting the arch 130 with resilient pressure. We believe that the arch cell 74 under the arch 130 also acts as a dynamic pump enhancing the flow of blood in the foot 62 and leg which may well be a source of nitric oxide.

The tendon cell 72 envelopes the back of the heel 62 and thus the Achilles tendon 63. The inflation of the tendon cell 72 is confined by the V-shaped metal support 86 that prevents outward expansion and directs the energy of pulsation inwardly to the sides of the Achilles tendon 63. As previously stated, the metal comprising the support 86 is sufficiently flexible to permit manual reshaping to conform to the angle of the individual's heel 62 and the Achilles tendon 63 but rigid enough to withstand the pressure of the inflated tendon cell 72 without distortion. The preferred material for the support is aluminum alloy 6061T4 in 0.32 inch gauge.

The pressure from the tendon cell 72 is confined to the sides of the Achilles tendon 63 instead of the back of the Achilles tendon 63 by dividing the tendon cell 74 into two lateral compartments 94, 96 which are, as previously discussed, separated by a medial uninflated zone 92. Both the lateral compartment 94 and the lateral compartment 96 are inflated with air flowing through the inlet tube 106 and traversing but not inflating the uninflated zone 92. Without the uninflated zone 92, inflation would cause the support 86 to push away from the heel 62. Under such conditions, compression against the sides of the Achilles tendon 63 would be lost because the only counter force to the rearward expansion of the tendon cell 72 would be the inner side of the first and second ankle straps 24, 46 wrapped around the ankle 60. The ankle straps 24, 26 would have to be unacceptably tight and inelastic to be effective as a counter force.

To utilize the Achilles wrap 10, the wrap 10 is laid open on a surface. The tendon cell 72 is attached to the first and second ankle straps 24, 26 by engaging the strips VELCRO type 88, 89 on the tendon cell 72 to the first and second ankle straps 24, 26, respectively. The support 86 is bent to accommodate the angle presented by the heel 62 of the foot. The arch cell 74 is attached to the foot strap 12 by engaging the VELCRO type strip 116 with the woven filament material of the foot strap 12. The arch cell 74 should be positioned so the neck portions 121, 122 of the cell 74 are pointing toward the inside of the foot 64. Once the arch cell 74 is positioned on the foot strap 12, the ankle strap is secured around the ankle 60 so the tendon cell 72 receives the Achilles tendon 63 of the foot. The ankle strap is secured around the ankle by engaging the hooks on the tabs 28, 34 to the woven filament material of the ankle straps 24, 26. Because the tabs 28, 34 with the plurality of hooks are facing in opposite directions, the tab 34 on the second ankle strap 26 with the hooks facing outwardly goes in the inside of the first ankle strap 24 and the hooks on the tab 28 of the first ankle strap 24 facing inwardly is applied to the outside of the second ankle strap 26. Therefore, both tabs 28, 34 are secured to respective ankle straps 24, 26. No weight should be put on the arch cell 74 until the ankle straps 24, 26 are secured.

Upon securing the ankle straps 24, 26, the foot 64 can be placed on the arch cell 74 and the foot strap 12 secured around the foot. The first end 14 and the second end 16 of the foot strap 12 each have tabs 18, 20 with a plurality of hooks facing in opposite directions, so the second end 16 is positioned inwardly of the first end 14. Thus, the hooks on tab 18 on the first end 14 engage the woven filament material on the second end 16 and the hooks on the tab 20 on the second end 16 engage the woven filament material of the first end 14. After the Achilles wrap 10 is wrapped around the foot 64 and secured, the inlet tube 106 can be coupled to the outlet tube 23 via the connector 124. By applying pressure to and removing pressure from the arch cell 74, the tendon cell 72 applies dynamic pressure to the heel 62 as previously described.

It will be appreciated that the detailed description and the examples relate to the preferred embodiment by way of example only. Many variations of the invention will be obvious to those knowledgeable in the field, and such obvious variations are within the scope of the invention as described and claimed, whether or not expressly described.

What is claimed is:

1. A device for applying dynamic pressure to the Achilles tendon of a human foot comprising:
   a wrap with at least one strap for detachably fastening the wrap around the foot and around an adjacent ankle;
   an arch cell containing a volume of air positioned within said wrap so as to be located under the arch of the foot, said arch cell being in communication with a conduit member, said arch cell being fabricated from a flexible material, so that upon application of external pressure to said arch cell air is expelled through said conduit member;
   an Achilles tendon cell containing a volume of air, said tendon cell being operatively connected to said arch cell via said conduit member, said tendon cell being positioned within said wrap so as to be located against the Achilles tendon, said tendon cell being fabricated from a flexible material, so that upon expelling of air from said arch cell through said conduit member into said tendon cell, said tendon cell exerts a dynamic pressure against the Achilles tendon;
   wherein said tendon cell comprises two walls sealed together along common edges thereof on all but one edge to form a pocket; and
   wherein said tendon cell includes a generally V-shaped support in said pocket, said support including a medial vertex portion joining two leg portions, whereby said support may be readily manually shaped to change the angle between the leg portions of the support.

2. The device of claim 1 wherein said arch cell contains a foam pad whereby upon removal of said exterior pressure from said arch cell, air is drawn from said tendon cell through said conduit member into said arch cell.

3. The device of claim 1 wherein said tendon cell includes a hermetically sealed chamber for positioning on at least one side of the Achilles tendon.

4. The device of claim 3 wherein said tendon cell further includes a noninflatable medial zone for positioning on the back of the Achilles tendon.

5. The device of claim 1 wherein said at least one strap is fabricated from a flexible, stretchable material which is attachably engageable by a plurality of hooks.

6. The device of claim 5 wherein said at least one strap comprises a woven filament material.

7. The device of claim 5 wherein said at least one strap has a first end and a second end, a first tab containing a plurality of hooks is connected to said first end and a second tab containing a plurality of hooks is connected to a second end and said hooks on said first end are facing in an opposite direction than said hooks on said second end.

8. The device of claim 1 wherein said wrap further comprises a foot strap for wrapping around the foot and a heel strap for enveloping the heel, said foot strap having a proximal side and said heel strap having a distal side, a portion of said proximal side of said foot strap being connected to a portion of said distal side of said heel strap.

9. The device of claim 8 wherein said heel strap has a first end and a second end and said wrap further includes a first ankle strap and a second ankle strap, the first end of said heel strap is connected to a side of said first ankle strap and said second end of said heel strap is connected to a side of said second ankle strap.

10. The device of claim 9 wherein said first ankle strap has a first end and a second end and said second ankle strap has a first end and a second end, said second end of said first ankle strap is connected to a second end of said second ankle strap.

11. The device of claim 10 wherein said second end of said first ankle strap is connected to said second end of said second ankle strap to define an angle between said first ankle strap and said second ankle strap.

12. The device of claim 1 wherein said conduit member comprises two tubes connectable together by a coupling member, said first tube is in communication with said arch cell and said second tube is in communication with said tendon cell.

13. The device of claim 1 wherein said tendon cell includes first and second lateral compartments separated by a medial non-inflatable zone.

14. The device of claim 13 further including a substantially rigid support having a medial portion joining first and second leg portions and being in respective supporting engagement with said first and second lateral compartments thereby to hold the tendon cell in supporting engagement with the wearer's Achilles tendon upon inflation of the tendon cell.

15. A device for applying dynamic pressure to the Achilles tendon of a human foot comprising:
   a wrap with at least one strap for detachably fastening the wrap around the foot and around an adjacent ankle;
   an arch cell containing a volume of air positioned within said wrap so as to be located under the arch of the foot, said arch cell being in communication with a conduit member, said arch cell being fabricated from a flexible material, so that upon application of external pressure to said arch cell is expelled through said conduit member;
   an Achilles tendon cell containing a volume of air, said tendon cell being operatively connected to said arch cell via said conduit member, said tendon cell being positioned within said wrap so as to be located again the Achilles tendon, said tendon cell being fabricated from a flexible material, so that upon expelling of air from said arch cell through said conduit member into said tendon cell, said tendon cell exerts a dynamic pressure against the Achilles tendon;
   wherein said wrap further comprises a foot strap for wrapping around the foot and a heel strap for enveloping the heel, said foot strap having a proximal side and said heel strap having a distal side, a portion of said proximal side of said foot strap being connected to a portion of said distal side of said heel strap;
   said tendon cell including a hermetically sealed chamber for positioning on at least one side of the Achilles tendon and further including a noninflatable medial zone for positioning on the back of the Achilles tendon.

16. The device of claim 15 wherein said arch cell contains a foam pad whereby upon removal of said exterior pressure from said arch cell, air is drawn from said tendon cell through said conduit member into said arch cell.

17. The device of claim 15 wherein said tendon cell comprises two walls sealed together along common edges thereof on all but one edge to form a pocket.

18. The device of claim 15 wherein said at least one strap is fabricated from a flexible, stretchable material which is attachably engageable by a plurality of hooks.

19. The device of claim 18 wherein said at least one strap comprises a woven filament material.

20. The device of claim 18 wherein said at least one strap has a first end and a second end, a first tab containing a plurality of hooks is connected to said first end and a second tab containing a plurality of hooks is connected to a second end and said hooks on said first end are facing in an opposite direction than said hooks on said second end.

21. The device of claim 15 wherein said conduit member comprises two tubes connectable together by a coupling member, said first tube is in communication with said arch cell and said second tube is in communication with said tendon cell.

22. A device for applying dynamic pressure to the Achilles tendon of a human foot comprising:
- a wrap with at least one strap for detachably fastening the wrap around the foot and around an adjacent ankle;
- an arch cell containing a volume of air positioned within said wrap so as to be located under the arch of the foot, said arch cell being in communication with a conduit member, said arch cell being fabricated from a flexible material, so that upon application of external pressure to said arch cell air is expelled through said conduit member;
- an Achilles tendon cell containing a volume of air, said tendon cell being operatively connected to said arch cell via said conduit member, said tendon cell being positioned within said wrap so as to be located against the Achilles tendon, said tendon cell fabricated from a flexible material, so that upon expelling of air from said arch cell through said conduit member into said tendon cell, said tendon cell exerts a dynamic pressure against the Achilles tendon;
- wherein said wrap further comprising a foot strap for wrapping around the foot and a heel for enveloping the heel, said foot strap having a proximal side and said heel strap having a distal side, a portion of said proximal side of said foot strap being connected to a portion of said distal side of said heel strap;
- said tendon cell comprising two walls sealed together along common edges thereof on all but one edge to form a pocket and wherein said tendon cell includes further including a generally V-shaped support in said pocket, said support including a medial vertex portion joining two leg portions, whereby said support may be readily manually shaped to change the angle between the leg portions of the support.

23. A device for applying dynamic pressure to the Achilles tendon of a human foot comprising:
- a wrap with at least one strap for detachably fastening the wrap around the foot and around an adjacent ankle;
- an arch cell containing a volume of air positioned within said wrap so as to be located under the arch of the foot, said arch cell being in communication with a conduit member, said arch cell being fabricated from a flexible material, so that upon application of external pressure to said arch cell air is expelled through said conduit member;
- an Achilles tendon cell containing a volume of air, said tendon cell being operatively connected to said arch cell via said conduit member, said tendon cell being positioned within said wrap so as to be located against the Achilles tendon, said tendon cell being fabricated from a flexible material, so that upon expelling of air from said arch cell through said conduit member into said tendon cell, said tendon cell exerts a dynamic pressure against the Achilles tendon;
- wherein said wrap further comprises a foot strap for wrapping around the foot and a heel strap for enveloping the heel, said foot strap having a proximal side and said heel strap having a distal side, a portion of said proximal side of said foot strap being connected to a portion of said distal side of said heel strap; and
- wherein said heel strap has a first end of a second end and said wrap further includes a first ankle strap and a second ankle strap, the first end of said heel strap is connected to a side of said first ankle strap and said second end of said heel strap is connected to a side of said second ankle strap.

24. The device of claim 23 wherein said first ankle strap has a first end and a second end and said second ankle strap has a first end and a second end, said second end of said first ankle strap is connected to a second end of said second ankle strap.

25. The device of claim 24 wherein said second end of said first ankle strap is connected to said second end of said second ankle strap to define an angle between said first ankle strap and said second ankle strap.

26. A device for applying dynamic pressure to the Achilles tendon of a human foot comprising:
- a wrap with at least one strap for detachably fastening the wrap around the foot and around an adjacent ankle;
- an arch containing a volume of air positioned within said wrap so as to be located under the arch of the foot, said arch cell being in communication with a conduit member, said arch cell being fabricated from a flexible material, so that upon application of external pressure to said arch cell air is expelled through said conduit member;
- an Achilles tendon cell containing a volume of air, said tendon cell being operatively connected to said arch cell via said conduit member, said tendon cell being positioned within said wrap so as to be located against the Achilles tendon, said tendon cell being fabricated from a flexible material, so that upon expelling of air from said arch cell through said conduit member into said tendon cell, said tendon cell exerts a dynamic pressure against the Achilles tendon;
- wherein said wrap further comprises a foot strap for wrapping around the foot and a heel strap for enveloping the heel, said foot strap having a proximal side and said heel strap having a distal side, a portion of said proximal side of said foot strap being connected to a portion of said distal side of said heel strap; and
- wherein said tendon cell includes first and second lateral compartments separated by a medial non-inflatable zone.

27. The device of claim 26 further including a substantially rigid support having a medial portion joining first and second leg portions and being in respective supporting engagement within said first and second lateral compartments thereby to hold the tendon cell in supporting engagement with the wearer's Achilles tendon upon inflation of the tendon cell.

28. A device for applying dynamic pressure to the Achilles tendon of a human foot comprising:
- a wrap with at least one strap for detachably fastening the wrap around the foot and around an adjacent ankle;
- an arch cell containing a volume of air positioned within said wrap so as to be located under the arch of the foot, said arch cell being in communication with a conduit member, said arch cell being fabricated from a flexible material, so that upon application of external pressure to said arch cell air is expelled through said conduit member;

an Achilles tendon cell containing a volume of air, aid tendon cell being operatively connected to said arch cell via said conduit member, said tendon cell being positioned within said wrap so as to be located against the Achilles tendon, said tendon cell being fabricated from a flexible material, so that upon expelling air from said arch cell through said conduit member into said tendon cell, said tendon cell exerts a dynamic pressure against the Achilles tendon;

said tendon cell including first and second lateral compartments separated by a medial non-inflatable zone; and a substantially rigid support having a medial portion joining first and second leg portions and being in respective supporting engagement with said first and second compartments thereby to hold the tendon cell in supporting engagement with the wearer's Achilles tendon upon inflation of the tendon cell.

29. The device of claim 28 wherein said arch cell contains a foam pad whereby upon removal of said exterior pressure from said arch cell, air is drawn from said tendon cell through said conduit member into said arch cell.

30. The device of claim 28 wherein said tendon cell includes a hermetically sealed chamber for positioning on at least one side of the Achilles tendon.

31. The device of claim 30 wherein said noninflatable medial zone is positionable on the back of the Achilles tendon.

32. The device of claim 28 wherein said tendon cell comprises two walls sealed together along common edges thereof on all but one edge to form a pocket.

33. The device of claim 32 wherein said substantially rigid support is a generally V-shaped support in said pocket, said medial portion includes a medial vertex portion joining said leg portions, whereby said support may be readily manually shaped to change the angle between the leg portions of the support.

34. The device of claim 28 wherein said strap is fabricated from a flexible, stretchable material which is attachably engageable by a plurality of hooks.

35. The device of claim 34 wherein said strap comprises a woven filament material.

36. The device of claim 34 wherein said strap has a first end and a second end, a first tab containing a plurality of hooks is connected to said first end and a second tab containing a plurality of hooks is connected to a second end and said hooks on said first end are facing in an opposite direction than said hooks on said second end.

37. The device of claim 28 wherein said wrap further comprises a foot strap for wrapping around the foot and a heel strap for enveloping the heel, said foot strap having a proximal side and said heel strap having a distal side, a portion of said proximal side of said foot strap being connected to a portion of said distal side of said heel strap.

38. The device of claim 37 wherein said heel strap has a first end and a second end and said wrap further includes a first ankle strap and a second ankle strap, the first end of said heel strap is connected to a side of said first ankle strap and said second end of said heel strap is connected to a side of said second ankle strap.

39. The device of claim 38 wherein said first ankle strap has a first end and a second end and said second ankle strap has a first end and a second end, said second end of said first ankle strap is connected to a second end of said second ankle strap.

40. The device of claim 39 wherein said second end of said first ankle strap is connected to said second end of said second ankle strap to define an angle between said first ankle strap and said second ankle strap.

41. The device of claim 28 wherein said conduit member comprises two tubes connectable together by a coupling member, said first tube is in communication with said arch cell and said second tube is in communication with said tendon cell.

* * * * *